United States Patent [19]

Maggioni et al.

[11] Patent Number: 4,816,592

[45] Date of Patent: Mar. 28, 1989

[54] PROCESS FOR THE PRODUCTION OF CERTAIN 2,3-DIHYDRO-BENZOFURAN DERIVATIVES

[75] Inventors: Paolo Maggioni, Montevecchia; Francesco Minisci, Milan; Mariano Correale, Bonate Sotto, all of Italy

[73] Assignee: Enichem Sintesi Spa, Palmero, Italy

[21] Appl. No.: 575,544

[22] Filed: Jan. 31, 1984

[30] Foreign Application Priority Data

Feb. 4, 1983 [IT] Italy .................. 19429 A/83

[51] Int. Cl.$^4$ .......................................... C07D 307/86
[52] U.S. Cl. ................................................. 549/462
[58] Field of Search ....................................... 549/462

[56] References Cited

U.S. PATENT DOCUMENTS

| | | | |
|---|---|---|---|
| 2,681,371 | 6/1954 | Gaydasch et al. | 549/462 |
| 3,474,170 | 10/1969 | Scharpf | 549/470 |
| 4,297,284 | 10/1981 | Michelet | 549/462 |
| 4,321,204 | 3/1982 | Büttner et al. | 549/462 |
| 4,324,731 | 4/1982 | Michelet et al. | 549/462 |
| 4,380,654 | 4/1983 | Franko-Filipasic et al. | 549/462 |

OTHER PUBLICATIONS

Bartz et al, J.A.C.S., vol. 57, pp. 371–376 (1935).
Olah, Friedel-Crafts & Related Reactions, vol. 1, pp. 25–27, 202, 203, 258, 259, 289, and 307 (1963).
Mustafa, Benzofurans, Wiley Publishers, pp. 144 and 145 (1974).

Primary Examiner—Mary C. Lee
Assistant Examiner—Bernard I. Dentz
Attorney, Agent, or Firm—Parkhurst, Oliff & Berridge

[57] ABSTRACT

A process for the production of benzofuran derivatives having the general formula,

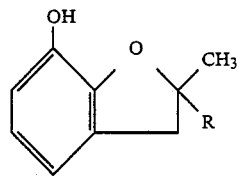

wherein R is alkyl, in particular of 2,3-dihydro-2,2-dimethyl benzofuran-7-ol, starting from pyrocatechol ethers in one step operation.

The process essentially consists of heating a solution of pyrocatechol ether in an inert organic solvent in the presence of a catalyst comprising metals of 3° and 4° group of the Periodic System in form of carboxylates or of modified zeolites.

The products are known intermediates for the production of insecticides.

17 Claims, No Drawings

PROCESS FOR THE PRODUCTION OF CERTAIN 2,3-DIHYDRO-BENZOFURAN DERIVATIVES

This invention concerns a new process for the production of benzofuran derivatives with the formula,

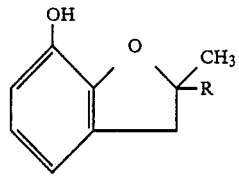
(A)

where R is an alkyl radical with 1 to 6 atoms of C. More specifically, this invention concerns a new process for the production of benzofuran derivatives from pyrocatechol ethers, particularly from monoethers having the formula,

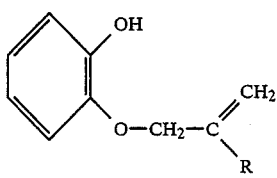
(B)

where R is as previously defined, by means of direct transposition and cyclisation in a single phase, in the presence of catalysts comprising metals of 3° and 4° group of the Periodic System in form of carboxylates or of modified zeolites.

All of the catalysts belonging to the catalyst class defined above give practically equivalent results.

The choice of using a soluble metallic salt or an insoluble zeolite means working in either a homogeneous or heterogeneous phase and depends, more or less, on any problems regarding the separation.

Notwithstanding its general character and considering the above defined limitations, the process of this invention is a particularly important one, and was specifically developed for the preparation of 2,3-dihydro-2,2-dimethyl-benzofuran-7-ol, which is the intermediate (I) for the preparation of carbofuran (II), a known and widely-used polyvalent insecticide.

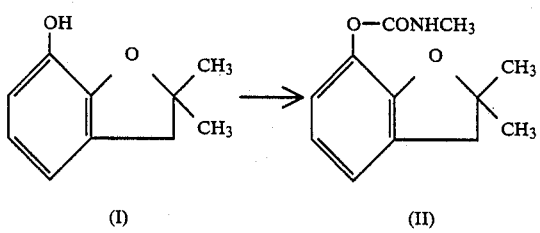

To date, many processes for the preparation of compound (I) have been proposed. All these processes involve different procedures but they all comprise three basic phases: (1) the monoetherification of pyrocatechol using methallyl chloride, (2) the thermal transposition of the methallylic monoether of pyrocatechol to ortho-methallylpyrocatechol and (3) the cyclisation of the ortho-methallylpyrocatechol to compound (I).

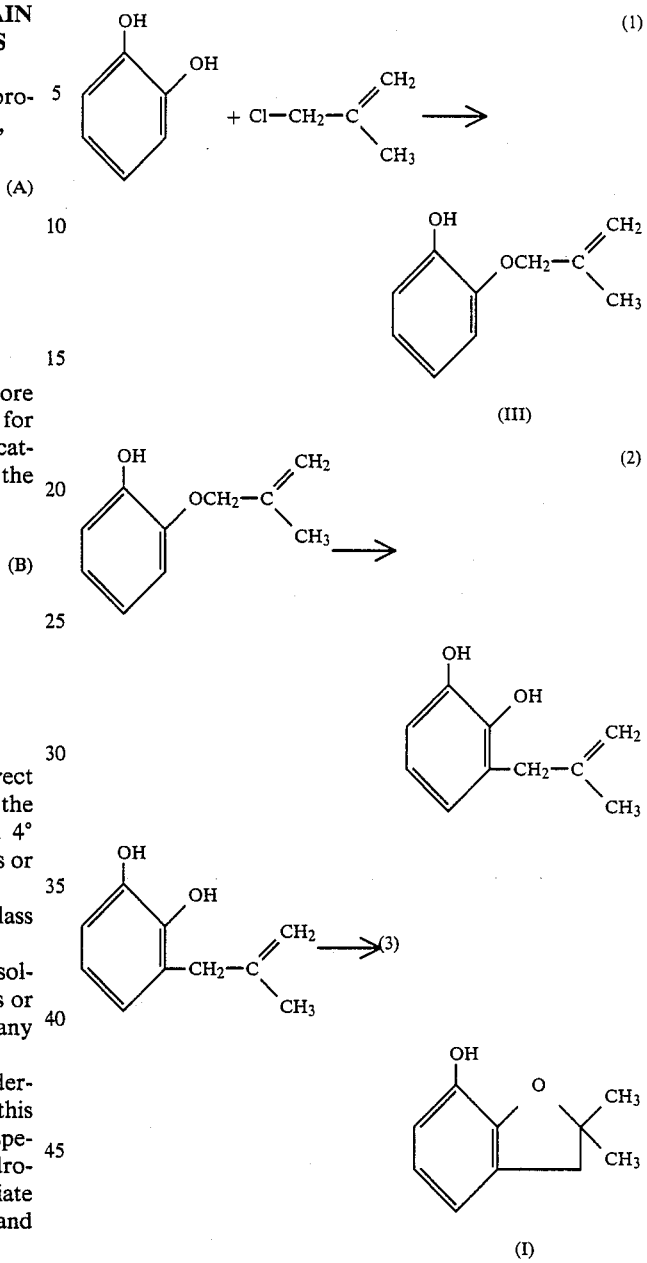

Now we have discovered, and it is one of the objects of this invention, that, with the phase-(1) preparation of the methallylic monoether of pyrocatechol remaining unchanged—which can be made by any known process—it is possible the cyclization of compound (III) to compound (I), directly, in one single phase, under moderated conditions, when it is heated in the presence of a catalyst as previously defined. The advantage of this new process over the known processes is immediately evident from the fact that one whole operative phase has been completely eliminated, while the operative conditions are considerably more bland than with the usual cyclisations. The simplification of the process, in terms of lower enery requirements, a decrease in the amount of reagent needed and less required equipment, is quite considerable and provides a substantial cost cut. The process, further more, can be made to provide high conversions, even very close to 100%, and a selectivity which exceeds 80%. This, of course, makes separation and purifying simpler, thus further reducing costs.

As mentioned, the new process described in this invention takes place homogeneously in the presence of an organic solvent or mixture of organic solvents which are inert under the reaction conditions but are able to completely dissolve the compound (III). Suitable solvents, for example, could be aprotic solvents, which are relatively weak bases, such as aliphatic hydrocarbons, or aromatic hydrocarbons and their derivatives—which are also weak bases—such as, for example, the halogen and nitrogen derivatives and other similar substances.

From this point of view, it is particularly advantageous to conduct the previously mentioned phase (1)—the monoetherification of the pyrocatechol—in accordance with the Applicant's European Patent Application No. 92,102, published Oct. 26, 1983. According to this Patent Application, the pyrocatechol ether is made from pyrocatechol and methallyl chloride in solution with organic solvents—which can be essentially the same solvents described in this invention—in the presence of a phase-transferring catalyst and a solid, inorganic base. When the reaction is completed, all that is required for proceding with the new process is the separation of the base and phase-transferring catalyst and the addition of the catalyst described in this invention to the obtained clear solution.

The catalysts which are most suitable for the new process are the salts of titanium, aluminum, tin and the zeolites modified with ions of metals belonging to 3° or 4° group of Periodic System.

The ratio between the catalyst and the ether (III) should be preferably between 0.0005 and 0.05 by weight. The temperature for the reaction should be held between 60° and 220° C. and, preferably between 80° and 180° C.

The time required for the reaction depends on the temperature and amount of catalyst. Optimum results can be obtained, however, within 60–90 minutes.

The product (I) is separated from the solution and purified according to known techniques.

The catalyst may be recovered and reused. This recovery is particularly simple in the case where the insoluble zeolites are used.

By way of illustration, but without thereby implying any limitations of any kind, the following practical examples of this invention are given.

EXAMPLE 1

20.4 g of methallylic monoether of pyrocatechol, 11.5 mg of titanium stearate and 100 ml of decalin are put inside a flask which incorporates a mixing and cooling means. The mixture is heated to 140° C. and held there for 3 hr and 30 minutes while the mixture is continuously stirred. The organic phase is analyzed by means of gas chromatography.

Conversion 85% and 73% yield of 2,3-dihydro-2,2-dimethyl-7-hydrohybenzofuran.

Under the same reaction conditions but without the use of a catalyst, no appreciable reaction takes place and the original product remains unchanged.

EXAMPLE 2

The same procedure is used as in Example 1, except that a temperature of 100°0 C. is held for four hours.

Conversion 70% and 68% yield of dihydro-2,2-dimethyl-7-hydroxybenzofuran.

EXAMPLE 3

The same procedure is used as in Example 1, except that 20 mg of titanium stearate are used and the mixture is held at 140° C. for 5 hours.

Conversion 80% and 50% yield of 2,3-dihydro-2,2-dimethyl-7-hydroxybenzofuran.

EXAMPLE 4

20 g of methallylic monoether of pyrocatechol, 11.5 mg of titanium stearate and 93 ml of xylenes (mixtures or ortho, meta and para) are put inside a flask which incorporates a mixing and cooling means. The mixture is heated to a temperature of 140° C. and held there for 3 hours and 30 minutes while the mixture is continuously stirred.

The organic phase is analyzed by means of gas chromatography.

Conversion 99% and 56% yield of 2,3-dihydro-2,2-dimethyl-7-hydroxybenzofuran.

Under the same conditions, but without the use of a catalyst, the methallylic monoether of pyrocatechol remains unchanged.

EXAMPLE 5

The same procedure as in Example 4, except that anisole is used instead of the xylenes, and carrying out the reaction at 165°+170° C.

Conversion 100% and 60% yield of 2,3-dihydro-2,2-dimethyl-7-hydroxybenzofuran. When no catalyst is used, there is no reaction.

EXAMPLE 6

16.6 g of methallylic monoether of pyrocatechol and 2.8 g of titanium modified zeolite in 90 ml of decalin are put inside a flask which incorporates a mixing and a cooling mean.

The mixture is heated up to 140° C. for 2 hours and 30 minutes under stirring.

The organic phase is analysed by means of gas chromatography.

Conversion=80 percent and 81 percent yield of 2,3-dihydro-2,2-dimethyl-7-hydroxybenzofuran.

EXAMPLE 7

The same procedure as in Example 6, except that the reaction is protracted for 4 hours.

Conversion 99.6% and 69% yield of 2,3-dihydro-2,2-dimethyl-7-hydroxybenzofuran.

When no catalyst is present there is no remarkable reaction.

EXAMPLE 8

18 g of methallylic monoether of pyrocatechol, 0.34 g of aluminium stearate and 100 ml of decalin are put into the type of flask used in the previous examples and the mixture is heated to 180° C. and held at that temperature for 1 hour while the mixture is continually stirred. The mixture is then allowed to cool and analyzed by means of gas chromatography.

Conversion 70% and 84% yield.

When no catalyst is present, there is practically no reaction under these conditions.

EXAMPLE 9

The same procedure as in Example 8, except that the mixture is heated to 180° C. and held there for 4 hours.

Conversion 98.6% and 70% yield.

Under the same conditions, when no catalyst is present, only traces of benzofuranol are produced.

EXAMPLE 10

9.8 g of methallylic monoether of pyrocatechol, 0.18 g of aluminium stearate and 47 ml of xylenes (mixture of ortho, meta and para) are put into the type of flask used in the previous examples.

The mixture is heated to 140° C. and held there for 5 hours while the mixture is stirred under condensate reflux. Extraction is done with ethyl acetate and the organic phase is analyzed by means of gas chromatography.

Conversion 86% and 54% yield.

Under the same conditions but without the use of a catalyst, the original product remains unchanged.

EXAMPLE 11

The same procedure as in Example 8, except that Linpar 10 (C10 linear paraffins) is used as a solvent, the temperature being held at 180° C. for 1 hour.

Conversion 88% and 76% yield.

EXAMPLE 12

18.6 g of methallylic monoether of pyrocatechol, 0.13 g of Sn oxalate, and 100 ml of decalin are put into a flask of the type used in the foregoing examples. The mixture is heated to a temperature of 140° C. and held there for 1 hour and 30 minutes while continuously stirring the mixture. The mixture is then allowed to cool to ambient temperature and is analyzed by means of gas chromatography.

Conversion 96% and 51% yield.

Under the same conditions, there is no reaction when no catalyst is present.

We claim:

1. A process for the preparation of benzofuran derivatives having the formula:

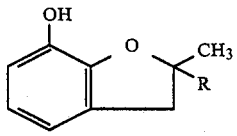

where R is an alkyl radical with 1–6 atoms of C, characterized by the fact that a pyrocatechol ether, having the formula:

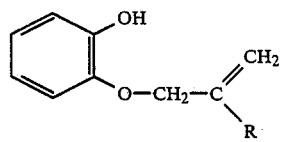

where R is as defined above, is put in solution with an inert, organic solvent in the reaction conditions in the presence of a catalyst comprising Al or Ti or Sn in the form of salt of carboxylic acid or of a zeolite modified by the cation of the same elements, said solution being then heated to a temperature ranging from 60° to 220° C.

2. A process, as in claim 1, in which the 2,3-dihydro-2,2-dimethylbenzofuran-7-ol, which has the formula,

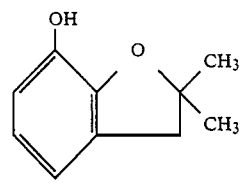

is prepared from methallylic ether of the pyrocatechol having the formula,

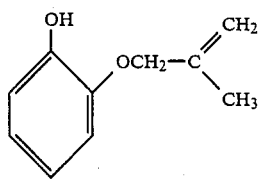

under the defined conditions.

3. A process, as in claim 1, in which the solvent is chosen from the group of aliphatic and aromatic hydrocarbons and their halogen and nitro derivatives.

4. A process, as in claim 1, in which the ratio, by weight, of catalyst and pyrocatechol ether is between 0.0005 and 0.05.

5. A process, as in claim 1, which is carried out in a homogeneous phase.

6. A process, as in claim 1, which is carried out in a heterogeneous phase.

7. A process according to claim 1, carried out at a temperature between 80° and 180° C.

8. A process for the preparation of a benzofuran derivative having the formula:

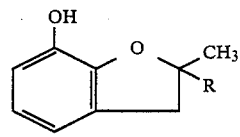

wherein R is an alkyl radical with 1–6 atoms of C, comprising heating at a temperature ranging from 60° to 220° C. a pyrocatechol ether, having the formula:

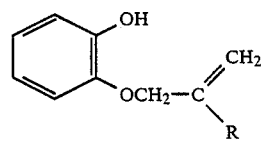

where R is as defined above, in the presence of an inert, organic solvent and a catalyst comprising a tin salt of a carboxylic acid or a zeolite modified by a tin cation.

9. A process for the preparation of benzofuran derivatives having the formula:

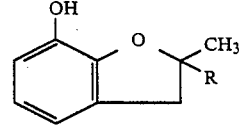

where R is an alkyl radical with 1-6 atoms of C, characterized by the fact that a pyrocatechol ether, having the formula:

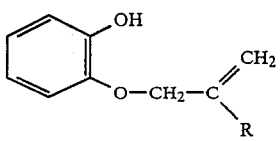

where R is as defined above, is put in solution with an inert, organic solvent in the reaction conditions in the presence of a catalyst comprising Al or Ti in the form of salt of carboxylic acid or of a zeolite modified by the cation of the same elements, said solution being then heated to a temperature ranging from 60° to 220° C.

10. A process according to claim 9, wherein said catalyst comprises Al in the form of salt of carboxylic acid or of a zeolite modified by the cation of Al.

11. A process according to claim 10, wherein said catalyst comprises Al carboxylate.

12. A process according to claim 11, wherein said Al carboxylate is Al stearate.

13. A process to according to claim 10, wherein said catalyst comprises Al modified zeolite.

14. A process according to claim 9, wherein said catalyst comprises Ti in the form of salt of carboxylic acid or of a zeolite modified by the cation of Ti.

15. A process according to clami 14, wherein said catalyst comprises Ti carboxylate.

16. A process according to claim 15, wherein said Ti carboxylate is Ti stearate.

17. A process according to claim 14, wherein said catalyst comprises Ti modified zeolite.

* * * * *